United States Patent [19]

Sawai et al.

[11] Patent Number: 5,118,503
[45] Date of Patent: Jun. 2, 1992

[54] COMPOSITION OBTAINED FROM RICE BRAN AND USE THEREOF

[75] Inventors: Kiichi Sawai; Masayasu Kurono; Hiromoto Asai; Takahiko Mitani; Naohisa Ninomiya; Eiji Furukawa, all of Aichi, Japan

[73] Assignee: Sanwa Kagaku Kenkyusho Co., Ltd., Nagoya, Japan

[21] Appl. No.: 359,894

[22] Filed: Jun. 1, 1989

[30] Foreign Application Priority Data

Jun. 9, 1988 [JP] Japan .................... 63-140385

[51] Int. Cl.⁵ ............................ A61K 35/78
[52] U.S. Cl. .................. 424/195.1; 424/76.1; 424/76.9
[58] Field of Search ........... 424/195.1, 76.9, 76.1, 424/76.21, 76.8; 426/18, 31; 435/267, 277

[56] References Cited

FOREIGN PATENT DOCUMENTS

| 15718 | 5/1972 | Japan | 424/76.9 |
| 5090 | 1/1979 | Japan | 426/31 |
| 7712 | 1/1981 | Japan | 424/195.1 |
| 4981 | of 1894 | United Kingdom | 426/31 |

*Primary Examiner*—John W. Rollins
*Assistant Examiner*—Anita Varma
*Attorney, Agent, or Firm*—Nikaido, Marmelstein, Murray & Oram

[57] ABSTRACT

Composition obtained from a rice bran, which comprises a filtrate of lactic fermented and aged material of the rice bran, the filtrate being an odorless pale yellow solution, having a salty taste, and solubility with water and alcohols, or a powderized substance of the filtrate, a process for the preparation of the composition, and use of the composition as a deodorant.

6 Claims, No Drawings

COMPOSITION OBTAINED FROM RICE BRAN AND USE THEREOF

BACKGROUND OF THE INVENTION

1. Field of the Invention

The present invention relates to a composition obtained from rice bran, process for the preparation thereof, and use of the composition as a deodorant.

The deodorizing composition according to the invention is orally administrated to animals inclusive of man, pet animals, domestic animals, experimental animals to substantially inhibit an appearance of various unpleasant or offensive smell of ozostomy, body odor, urine odor and others.

2. Related Arts

Exclusion of offensive smells is quite important, so as not to impede human communication or to keep good life environment.

When an animal is bred and more particularly, a cat, dog or the like animal is bred indoors, as a pet or experimental one, there are many cases of that so called "beastly or brute odor" due to body odor, smell of sweat, excretions of the animal floats indoor space and is adsorbed by textile interior decorarations, furnitures as well as architectural structures such as wall and pillar, so that the architecture per se will develop a strange and offensive odor. Such an odor shall not be so noticed by the breeder and concerned party, but gives strong unpleasant feelings to a third party.

Therefore, various measures have been proposed, but actually adopted measures are of ventilation and/or utilization of a spray- or stationary-type deodorant.

Among the conventional measures to the offensive odor, "ventilation" is too passive and its effectivity is quite low. While, almost all of the deodorants produce a masking of the offensive odor with a smell of a fragrant substance and as deodorants for pet animals, a specially prescribed one for the kind of pet animal has been marketed, but a smell depends on a personal liking or preference, so that the smell giving a nice feeling to a certain person may give unpleasant feeling to another person. In recent years, further, so-called "odorless-type deodorant" has been marketed, but this type one develops a certain strange or unfamiliar smell, although it is, in general, hard to identify a specific type of the smell.

SUMMARY OF THE INVENTION

A basic object of the invention is to provide a new type deodorant, which does not produce a masking effect, but can substantially decrease the unpleasant smell per se.

One of concrete objects of the invention is to provide a deodorizing composition for attaining the basic object.

Another concrete object of the invention is to provide a process for the preparation of such composition.

Still another concrete object of the invention lies in the use of the composition as the deodorant.

The present inventors have energetically studied to develop a new use on one of natural products of rice bran, namely a mixture of an embryo (or germ), an aleuron layer on an albumen, and a coating or skin forming an upper most layer of uncleaned rice (referred to as "hulled rice" or more usually as "brown rice"), based on that the rice bran can be obtained as by-product, when the brown rice is polished into cleaned or refined rice, is available with a reasonable low cost, and contains a great deal of nutritious ingredients, although it has already been utilized in various fields. As one of parts of the concerning studies, they have carried out nutritional physiological experiments on the rice bran to find that body odor and urine odor of experimental animals gradually decrease, when food containing the rice bran has been given. Then, they have tried to extract a substance showing such a deodorizing effect. As one of the trials, they have prepared a filtrate separated from fermented and aged material of the rice bran to give the substance to the experimental animals to confirm a fact that the odor of body and urine can remarkably decrease and it becomes into such an extent noticed as not offensive smell or odorless, so that the invention has been established.

According to the invention, therefore, the composition comprises a filtrate of lactic fermented and aged material of the rice bran, said filtrate being an odorless pale yellow solution, having a salty taste, solubility with water and alcohols as well as analytical values of

| | |
|---|---|
| crude protein | about 0.2%. |
| crude fat | about 0.1%. |
| crude fiber | not detected. |
| crude ash | about 4.5%. |
| moisture content | about 8.1%. |
| saccharinity | about 87.1%. |
| soidium content | about 1.9%. |
| phosphorus content | about 541 mg/100 g. and |
| pH | about 9.3. | or a powderized substance of the filtrate.

According to the process of the invention, the composition can be prepared by adding water to the rice bran to thermally treat the same, treating the same with enzyme to cause decomposition thereof, adding a lactic acid bacteria to cause a fermentation, obtaining a filtrate from culture medium, aging the filtrate, sterilizing the aged filtrate, and if necessary, powderizing the filtrate.

For carrying out the process of the invention, it is preferable to add the rice bran and water in weight ratio of about 50:50. The thermal treatment can be carried out with use of a suitable apparatus, for instance an autoclave and the treatment will be finished for about 30 minutes at 100° C. The enzymatical decomposition treatment can be carried out by adding a pectinase. The lactic fermentation is carried out by adding a conventional lactic acid bacteria to culture under aeration, but it is preferable to pre-set pH at a level of about 9.2–9.5. The required period of time for the cultivation is several days, for instance 3 days at about 35° C. The aging can be carried out by reserving the filtrate for about one month at about 5° C. The resulting aged or mellowed substance is filtered and the filtrate is sterilized. The sterilization may be carried out by a thermal treatment, for instance heating the filtrate for several minutes, for instance about 2 minutes at 100° C. The resulting sterilized solution has a pH of about 9.3.

The powderization of this original non-diluted solution or any diluted solution thereof can be carried out in a conventional manner, for instance, freeze-drying, spray-drying or a similar method.

The resulting original powder composition per se or a mixture thereof with another powder material can be used as a powder-type deodorant according to the invention. As the diluting powder material, a starch, dextrin or the like may be listed.

The liquid or powderized composition, or deodorant according to the invention is orally administered as it is, or in the form of food or drinking water which contains the composition. The oral administration of the composition apparently decreases an intensity of offensive odors such as body odor, odor of urine to be excreted from the administrated animal. However, a deodorizing mechanism of the composition has not yet been elucidated, since according to results of hematoscopy and uroscopy made on cats as experimental animals, a difference of significance between a test group and a control group has only been recognized in pH of the urine in the test group, excepting the odor of urine, and this difference in pH can, of course, be estimated by intake of the composition which is one of alkali substances.

DETAILED DESCRIPTION OF PREFERRED EMBODIMENTS

The invention will now be further explained in more detail with reference to Examples and Test Examples which were made on experimental animals, such as cats and dogs accepted as having a strong odor of body and urine, among pet animals.

EXAMPLE 1

To 1 kg of a rice bran commercially available in the market, 1 kg of water was added to stir the same and the resulting paste was charged in an autoclave kept therein for 30 minutes at 100° C. Then, pectinase (50 g) was added thereto and mixed to keep the same for 60–120 minutes at temperature of 25°–35° C. After naturally cooling, the resulting material was transferred to a cultivator and 20 g of commercially available lactic acid bacteria was planted to cultivate the same over 3 days at 34.5° C., under aeration. The culture medium was filtered and the resulting filtrate was aged for 30 days at 5° C. Then, the aged filtrate was sterilized by heating the same for 2 minutes at 100° C. to obtain the desired original filtrate (1400 ml). This filtrate has a pale yellow color, and shows a salty taste and a good solubility with water and alcohols.

The filtrate was analyzed to show following results.

| | |
|---|---|
| Crude protein | 0.2%, |
| Crude fat | 0.1%, |
| Crude fiber | not detected, |
| Crude ash | 4.5%, |
| Moisture content | 8.1%, |
| Saccharinity | 87.1%, |
| Soidium content | 1.9%, |
| Phosphorus content | 541 mg/100 g, and |
| pH | 9.3. |

Further, the original filtrate was diluted with water to prepare 40% (V/V) solution.

EXAMPLE 2

2140 g of the 40% solution obtained in Example 1 were spray-dried to obtain 140 g of powderized substance with 15.3 magnification in concentration.

To the resulting powder, dextrin was added and mixed therewith to obtain a powder composition diluted five folds.

EXAMPLE 3

To 1000 ml of the original filtrate obtained in Example 1, 300 ml of water and 760 g of dextrin were added and mixed. The resulting solution was spray-dried to obtain 750 g of a powderized substance, as desired composition.

TEST EXAMPLE 1 a) Experimental Animal

Cats were pre-breeded for 2 weeks and an inspection on general behavior and clinical inspections on excrements and blood were carried out. Among the animals to be judged as normal, the following were selected for experiments taking age, sex distinction, whether or not a castration had been done, into consideration.

Youth (age of about 1 year): 2 cats (each 1 for ♂ and ♀),

Matured (age of 2-6 years): 6 cats (each 3 for ♂ and ♀), and castrated: 2 cats (male).

Breeding Manner

Each experimental animal was separately bred within a cage in a breeding room kept at temperature of 23°–26° C. and humidity of about 60%. The breeding was carried out by supplying a dry-type cat food marketed by Kabushikikaisha Easter of Japan under their Trademark of "FARMY" in an amount of 3–4% of the body weight of each animal and over a constant period of time, namely 9:00–10:00 AM in each day. Each animal takes water freely.

c) Dosing Manner

As test samples, the original filtrate and 40% solution thereof obtained in Example 1 were selected. The test sample was orally given within 3 hours from completion of the feeding period of time, 1 time/day, and in an amount of 2 ml and 3 ml, respectively, in every day over the testing period of 2 weeks.

d) Testing Procedure i) Experimental animals and classification

Each of experimental animals was classified into the following 3 groups.

T-40: 40% solution dosing group;

T-100: the original filtrate dosing group, and

C: control group dosing no test sample.

Detail of the classification is shown in following Table 1.

TABLE 1

| Animal No. | Kind | Sex distinction | Group |
|---|---|---|---|
| 1 | Castrated | Male | T-40 |
| 2 | Matured | Female | T-100 |
| 3 | Castrated | Male | T-40 |
| 4 | Matured | Male | T-100 |
| 5 | Matured | Male | T-40 |
| 6 | Matured | Female | C |
| 7 | Matured | Female | C |
| 8 | Matured | Female | T-40 |
| 9 | Youth | Male | T-40 |
| 10 | Youth | Female | T-40 | ii) Content of tests

Each experimental animal was anesthetized by an administration of ketamine hydrochloride on the day just before the dosage of the test sample, and each day after 1 and 2 weeks from the begining of the dosage at the time of within 2:00 to 3:00 PM, so that 3 ml of blood were taken from carotid artery and urine was taken with use of a catheter (Tomcat catheter or No. 3 feeding tube).

As to the blood sample, hematocrit value (Ht), number of erythrocyte (RBC), number of leukocyte (WBC), total protein in serum (TP), GPT, GOT, serum alubmine (ALB), urea nitrogen in serum (BUN), calcium (Ca), inorganic phosphorus (P) and magnesium (Mg) were measured. As to urine sample, a smell thereof was judged immediately upon its taking and pH, protein, glucose, occult blood and urobilinogen were measured with use of "urorubsticks III" (Trademark) marketed by Miles Sankyo Co., Ltd. of Japan.

e) Results

As far as the blood inspections are concerned, some fluctuations can be recognized in hematocrit value and number of erythrocyte, but it was in the level of normal range and thus judged as not abnormal. A slight increase in the number of leukocyte was recognized at the time of second week inspection for one animal in T-40 group (Animal No. 10) and at the time of first and second week inspections for one animal in group C (Animal No. 6). All of animals showed values in the level of normal range on biochemical inspections of TP, GPT, GOT, serum albumin and BUN as well as electrolytic inspections of Ca, P and Mg.

Among the urine inspections, results on the smell are shown in following Table 2 and it has been judged that urogenous smell decreases in all of T-100 and T-40 groups. In the other inspections, an increase in pH of urine was recognized for 4 animals in T-40 group (Animal Nos. 1, 5. 8 and 10) and one animal in T-100 group (Animal No. 2). As to the urinous protein, 2 animals in T-100 group (Animal Nos. 2 and 4) and 2 animals in C group were judged as positive in all of its inspection times. As to the occult blood in urine, 1 animal in T-40 group (Animal No. 5) at the inspection time of before the dosage and 1 animal in C group (Animal No. 6) at every inspection time were judged as positive. No abnormal result can be recognized from results of the remaining inspections.

TABLE 2

| Animal No. | Before dose | After dose 7th | 14th |
| --- | --- | --- | --- |
| 1 | 1 | 3 | 3 |
| 2 | 1 | 3 | 3 |
| 3 | 1 | 3 | 3 |
| 4 | 1 | 3 | 3 |
| 5 | 1 | 3 | 3 |
| 6 | 1 | 1 | 1 |
| 7 | 1 | 1 | 1 |
| 8 | 1 | 3 | 3 |
| 9 | 1 | 3 | 3 |
| 10 | 1 | 3 | 3 |

Note (Urogenous smell):
1; Strong,
2: Weaken, and
3; Almost no smell f) Consideration It can be judged that the test sample solutions have a sufficient effectivity, since the urogenous smell was remarkably decreased or disappeared in each of the tested animals, on contrary to that on control animals.

The blood inspections and more particularly, the biochemical inspections did not show any value showing abnormal in heptic and renal functions. Further, no abnormal value was detected in the inspections of urine. It can also be judged, therefore, the test sample solutions have a high safety in use.

TEST EXAMPLE 2 a) Test Sample

The powderized and diluted composition obtained in Example 2.

b) Experimental Animal

Cats were pre-bleeded for 2 weeks and an inspection on general behavior and clinical inspection on excrements and blood were carried out. Among the animals to be judged as normal, matured male and female cats (cats of each sex) as well as youth male and female cats (1 cat of each sex), namely 10 heads in total were selected and classified into following 2 groups.

Group I: Mixed 1g of the powderized composition with each feed to be given 1 time/day, and Group II: Dissolved 1 g of the powderized composition in 3–5 ml of water and orally administered, after expiration of the feeding period of time.

Please note that 1 g of the powderized and diluted composition corresponds to 3 ml of the 40% solution obtained in Example 1.

c) Bleeding Manner

Same with those in Test Example 1.

d) Testing Procedure

As similar to that in Test Example 1, urine sample was taken with a catheter under anesthesia and judged immediately have a smell of the urine.

e) Results

Results are shown in following Table 3.

TABLE 3

| Animal No. | Group | Kind | Sex | Days from the first dose 1st | 3rd | 5th | 7th | 14th |
| --- | --- | --- | --- | --- | --- | --- | --- | --- |
| 1 | I | Matured | Male | 1 | 2 | 3 | 3 | 3 |
| 2 | I | Matured | Male | 1 | 3 | 3 | 3 | 3 |
| 3 | I | Matured | Female | 1 | 2 | 3 | 3 | 3 |
| 4 | I | Matured | Female | 1 | 3 | 3 | 3 | 3 |
| 5 | I | Youth | Male | 1 | 3 | 3 | 3 | 3 |
| 6 | II | Matured | Male | 1 | 1 | 3 | 3 | 3 |
| 7 | II | Matured | Male | 1 | 3 | 3 | 3 | 3 |
| 8 | II | Matured | Female | 1 | 3 | 3 | 3 | 3 |
| 9 | II | Matured | Female | 1 | 3 | 3 | 3 | 3 |
| 10 | II | Youth | Female | 1 | 3 | 3 | 3 | 3 |

In the Table,
1: No change in urogenous smell, in comparison with that before the dose,
2: Weaken in urogenous smell, and
3: Almost no smell of urine f) Consideration The urogenous smell decreases by continuous administration of the test composition over 3 days in all of the groups, and almost no smell will be noticed in 5th day from the first administration. This means that the composition shows its deodorizing effect, even if it added to the feed or to the drinking water. General observation on behavior, appetite and others during the testing period showed no abnormal result in veterinary judgement.

TEST EXAMPLE 3 a) Test Sample

The powderized composition obtained in Example 3.

b) Experimental Animal

Afganian dogs with long fur (age of about 2 years) were pre-bleeded for 2 weeks. Among the dogs, 6 dogs showing no abnormal data on general inspections were selected and classified into test and control groups (3 dogs each). To each animal in the test group, a feed containing the test sample composition in an amount of 0.25 g/kg (body weight of the animal) was given in 1 time/day and breeded for 1 week, in a breeding room kept at temperature of 23°–26° C.

c) Testing Procedure, and Results

A smelling test was carried out on sebaceous smell at the back and mane portions, by a professional panel (3 members) who will judge as "effective", when 2 or more members declare that there is significance difference between the test and control groups. As a result, all of the members declare that the smell in all of 3 dogs belonging to the Test Group rapidly decreases, as continuous dose of the test sample and becomes almost no noticeable one and therefore, that the test sample is effective as a deodorant for the animal.

What is claimed is:

1. A composition obtained from rice bran, which comprises a filtrate of lactic fermented and aged material of the rice bran, said filtrate being an odorless pale yellow solution, having a salty taste, solubility with water and alcohols as well as such analytical value of

| crude protein | about | 0.2%, |
|---|---|---|
| crude fat | about | 0.1%, |
| crude ash | about | 4.5%, |
| moisture content | about | 8.1%, |
| saccharinity | about | 87.1%, |
| sodium content | about | 1.9%, |
| phosphorus content | about | 541 mg/100 g. and |
| pH | about | 9.3. | or a dried solid product of said filtrate.

2. A composition obtained from a rice bran, which comprises a filtrate of lactic fermented and aged material of the rice bran, said filtrate being an odorless pale yellow solution, having a salty taste, solubility with water and alcohols as well as such analytical value of

| crude protein | about | 0.2%, |
|---|---|---|
| crude fat | about | 0.1%, |
| crude ash | about | 4.5%, |
| moisture content | about | 8.1%, |
| saccharinity | about | 87.1%, |
| sodium content | about | 1.9%, |
| phosphorus content | about | 541 mg/100 g. and |
| pH | about | 9.3. | or a dried solid product of said filtrate prepared by adding water to rice bran, thermally treating the same, adding an enzyme capable of decomposing rice bran to the same to cause decomposition, adding a lactic acid bacteria to cause fermentation, aging a filtrate of the fermented material, and sterilizing the aged filtrate to obtain a filtrate of lactic fermentated and aged material of rice bran, which sterilized filtrate is dried to obtain said dried product of said filtrate.

3. The composition of claim 2, wherein a weight ratio of said rice bran and water is about 50:50.

4. The composition of claim 2, wherein said enzyme is a pectinase.

5. The composition of claim 2, wherein said lactic fermentation is carried out by regulating the pH to 9.2–9.5, and cultivating for several days at temperature of about 35° C., under aeration.

6. The composition of claim 2, wherein said aging is carried out by allowing the filtrate to stand for about one month, at a temperature of about 5° C.

* * * * *